(12) United States Patent
Mazer

(10) Patent No.: US 6,906,038 B2
(45) Date of Patent: Jun. 14, 2005

(54) METHODS FOR ALLEVIATING MUCOSITIS

(75) Inventor: Terrence B. Mazer, Reynoldsburg, OH (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 10/152,434

(22) Filed: May 21, 2002

(65) Prior Publication Data

US 2003/0119755 A1 Jun. 26, 2003

Related U.S. Application Data

(60) Provisional application No. 60/315,598, filed on Aug. 29, 2001, now abandoned.

(51) Int. Cl.[7] .................. A01N 43/04; A61K 31/70; A23L 1/30
(52) U.S. Cl. .................. 514/23; 426/72; 426/74
(58) Field of Search .................. 514/23; 426/72, 426/74

(56) References Cited

U.S. PATENT DOCUMENTS

| | | | |
|---|---|---|---|
| 5,561,111 A | | 10/1996 | Guerrant et al. |
| 5,869,458 A | * | 2/1999 | Waite et al. .................. 514/23 |
| 6,183,784 B1 | * | 2/2001 | Read et al. .................. 424/535 |

OTHER PUBLICATIONS

Abbott Labratories Online, Pedialyte® Dosage Chart and Administration Guide, http://www.pedialyte.com/howpedialytecanhelp/dosage.cfm Copyright 1996.*

Comparison of Oral and Intravenous Hydration and Diuretic, Choice of Protecting Cisplatin Induced Nephrotoxicity, D. R. Kachhwaha et al; Indian Journal of Cancer (INDIA) Dec. 1996, 33 (4), p168–70, ISSN 0019–509X.

Diarrhea. Wadle KR, Nursing Service of Education, Veterans Administration Medical Center, Knoxville, IA; Nursing Clinics of North America (US) Dec. 1990, 25 (4) p 901–8, ISSN 0029–6465.

Oral Manifestations of Bone Marrow Transplantation, Carl W et al; Department of Dentistry and Maxillofacial Prosthetics. Roswell Park Memorial Institute, Buffalo, NY 14263 (US), 1985.

* cited by examiner

Primary Examiner—James O. Wilson
Assistant Examiner—Traviss C. McIntosh, III
(74) Attorney, Agent, or Firm—William J. Winter; Thomas D. Brainard

(57) ABSTRACT

The present invention is directed to a method for alleviating mucositis, sassociated with radiation and chemotherapy, via the administration of an oral rehydration solution.

21 Claims, No Drawings

METHODS FOR ALLEVIATING MUCOSITIS

This application is the non-provisional related to the provisional application, U.S. Ser. No. 60/315,598, which was filed on Aug. 29, 2001, now abandoned.

BACKGROUND

Chemotherapy and/or radiotherapy is effective at destroying tumors because it targets the most rapidly growing tissues. The mechanism involves impairment of DNA synthesis or interference with metabolic processes required for rapidly dividing cells. While tumor cells are selectively targeted by anticancer treatments, the most rapidly growing tissues of the host are also susceptible to these effects. The mucosal epithelium of the alimentary tract has one of the most rapid rates of cell division of any body tissue, and is therefore a major site of toxicity for anticancer regimens.

The linings of the mouth and esophagus are particularly sensitive to chemotherapy and radiation. The oral ulcerations characteristic of mucositis (also referred to as 'stomatitis') are a major clinical problem causing considerable pain, increased susceptibility to infection and inability to eat. Damage to the intestinal lining also occurs commonly in the small bowel, and less frequently in the large bowel, leading to severe diarrhea and pain. (Verdi C J 1993 Cancer therapy and oral mucositis. An appraisal of drug prophylaxis. Drug Safety 9:185–195; Sonis S T 1993 Oral complications of cancer chemotherapy In VT DeVita Jr., S Hellman and S A Rosenberg (ed) Cancer, Principles and Practice of Oncology, pp 2385–2394. Philadelphia, j B Lippencott Co).

In general, mucositis appears within 5 to 10 days of the drug or radiation treatment and can last several weeks. The severity of mucositis can limit subsequent doses of chemotherapy or radiation. Patients suffering mucositis may need several weeks, or more, of intravenous feeding as a result of the mouth ulcers, cramps, extreme pain, gut denuding, and severe diarrhea (Verdi 1993; Sonis 1993).

About 40% of all patients receiving chemotherapy develop significant mucositis. Incidences of up to 100% occur with some forms of chemotherapy or radiotherapy. Clinically significant mucositis develops with a range of standard chemotherapy drugs that are used, either alone or in combination, to treat various cancers including those of the colon, breast, prostate, head, neck and haemopoetic system. Examples of drugs that frequently cause direct mucositis include, but are not limited to, alkylating agents such as mechlorethamine, melphalan and busulphan, antimetabolites including cytarabine, floxuridine, 5-fluorouracil, mercaptopurine, methotrexate and thioguanine, cytotoxic drugs such as bleomycin, actinomycin-D, daunorubicin, cisplatin, etoposide, mitomycin, vinblastine and vincristine, and other chemotherapy drugs such as hyroxyurea and procarbazine (Sonis 1993). Direct exposure of the alimentary tract to high-dose radiotherapy, as occurs for example with total body irradiation, treatment of head and neck tumors or radiotherapy of abdominal tumors, will also cause a high incidence of mucositis.

One problem that is typically associated with mucositis is excessive weight loss. The damage inflicted upon the oral mucosa typically makes it painful for the patient to eat. This in turn leads to malnutrition, weight loss, and susceptibility to infections.

One current treatment for the pain associated with mucositis is oral morphine (Mayo Clinic). Oral morphine has several side effects including drowsiness, nausea, and severe constipation. These side effects can interfere with both continuation of treatment and recovery from treatment.

In addition to mucositis, loss of plasma potassium is typically associated with chemotherapy and radiation due to the diarrhea and vomiting described above. To avoid hypokalemia, potassium tablets are often given to the patient while they are undergoing chemotherapy. While these tablets minimize hypokalemia, they are very irritating to the patient's GI tract and can exacerbate the nausea and vomiting described above.

If the vomiting and diarrhea associated with chemotherapy becomes severe enough, patients can become severely dehydrated and experience electrolyte abnormalities. Such patients are often initiated on oral rehydration therapy after the occurrence of emesis and diarrhea. For example, Wadle reports that oral rehydration is typically initiated if chemotherapy patients are experiencing diarrhea, Nursing clinics of North America, December 1990, 25(4) page 901–908. Ippoliti also reports that after the occurrence of diarrhea, oral rehydration solutions should be used in cancer patients to replace any fluid loss, AM. j. Health-Syst. Pharm. August 1998 55/15 (1573–1580).

While the medical literature does describe using oral rehydration solutions (ORS) in cancer patients, their role in cancer therapy is similar to that of any patient experiencing diarrhea. ORS therapy is initiated after the onset of diarrhea and vomiting. The ORS is used to replace the water and electrolytes that the patient has lost. The medical literature does not describe the use of ORS to alleviate mucositis, especially oral mucesitits. Nor does the medical literature describe the prophylactic administration of ORS prior to the initiation of chemotherapy and/or radiation.

SUMMARY OF THE INVENTION

In accordance with the present invention, a new therapeutic use has been discovered for oral rehydration solutions (ORS). It has been discovered that ORS will alleviate mucositis in patients undergoing cancer chemotherapy and/ or radiation therapy. If consumed in sufficient quantities, the ORS will reduce reduce the physical discomfort the patient experiences from the mucositis. This reduction in pain will allow the patient to consume a greater number of calories and will help to alleviate the weight loss that is often associated with chemotherapy. Further, while the ORS will not prevent the occurrence of mucositis, it will help to speed the rate at which the lesions heal.

In order to gain these benefits, the ORS needs to be consumed in sufficient quantities. Typically, the patient will need to consume at least 500 milliters of ORS daily, and more typically up to about 2000 milliters. Consumption should be maintained until the pain from the mucositis has dissipated The ORS will also provide other benefits. The prophylactic administration will help to maintain plasma potassium levels in a normal range. This will decrease the need for potassium tablets and the gastrointestinal distress associated with these dosage forms. Further, maintaining an adequate state of hydration thru-out the patients treatment will help the patient maintain their strength and vigor leading to an enhanced quality of life.

DETAILED DESCRIPTION OF THE INVENTION

As used herein:
a) one milliequivalent (mEq) refers to the number of ions in solution as determined by their concentration in a given volume. This measure is expressed as the number of milliequivalents per liter (mEq/L). Milliequivalents may be converted to milligrams by multiplying mEq by the atomic weight of the mineral and then dividing that number by the valence of the mineral.

b) "ORS" or "ORS's" refers to oral rehydration solution(s). For the purposes of this invention, the term ORS should be construed as referring to any composition containing at a minimum, glucose, sodium and water; that would be considered suitable, by a medical professional, for use in rehydrating a patient who has experienced fluid and electrolyte loss due to diarrhea. Beverages such as sport drinks i.e. Gatorade®), soft drinks (i.e. Coca-Cola® or Pepsi®), or Kool-Aid®, should not be considered ORS's for the purpose of this invention. These beverages have a carbohydrate concentration in excess of 3.0 w/w % and would not function via the coupled transport mechanism described in detail below.

c) "mucositis" refers to toxic inflammatory reaction affecting the gastrointestinal tract for mouth to anus, which may result from exposure to chemotherapeutic or ionizing radiation. (NCI/PDQ Physician Statement: Oral complications of cancer and cancer therapy website 6/2000). Specific examples include oral mucositis, esopagitis, enterititis and colitis.

d) "oral mucositis" and stomatitis should be considered synonomus and refer to mucositis impacting the oral cavity.

e) Any reference to a numerical range in this application should be considered as being modified by the adjective "about".

f) Any numerical range should be considered to provide support for a claim directed to a subset of that range. For example, a disclosure of a range of from 1 to 10 should be considered to provide support in the specification and claims to any subset in that range (i.e. ranges of 2–9, 3–6, 4–5, 2.2–3.6, 2.1–9.9, etc.).

g) Any reference in the specification or claims to a quantity of an electrolyte should be construed as referring to the final concentration of the electrolyte in the ORS. Tap water often contains residual sodium, chlorine, etc. A value of 40 mEq of sodium, in this application, means that the total sodium present in the ORS equals 40 mEq, taking into account both added sodium as well as the sodium present in the water used to manufacture the ORS. This holds true for all electrolytes.

Oral rehydration solutions are well known to medical professionals such as physicians, pharmacists, nurses, dieticians, etc. Oral rehydration solutions (ORS) are now routinely utilized throughout the world to correct the fluid and electrolyte losses associated with diarrhea. They are used most prevalently in pediatric populations.

The principle underlying oral rehydration is the phenomenon of coupled transport. The presence of glucose in the ORS increases the absorption of sodium by the body. Every glucose molecule that crosses the intestinal epithelium brings a sodium ion with it, raising the concentration of ions in the blood stream and pulling water out of the gut. The exact concentration of glucose in the oral fluid is very important. Sodium absorption improves as the glucose concentration of the oral fluid is increased up to about 2.5% w/w. At higher concentrations, the glucose can no longer be efficiently absorbed leading to a net reduction in sodium and water absorption. In fact, higher concentrations of glucose increase the osmotic load in the gut, which pulls water out of the blood stream. This leads to a net loss of fluids and electrolytes which further exacerbates dehydration.

The World Health Organization recommended that an ORS contain 90 mEq of sodium per liter, 20 mEq of potassium per liter, 30 mEq carbonate per liter and 111 mM of glucose per liter. Other ORS's containing lower amounts of sodium have been demonstrated to be equally effective. For example, the American Academy of Pediatrics Committee on Nutrition recommendation for ORS is 40–60 mEq/L sodium, 20 mEq/L potassium, and 2.0–2.5 wt./wt. % carbohydrate.

The ORS useful in this invention will contain all the necessary electrolytes and levels thereof required by the United States Food and Drug Administration for oral rehydration formulations sold in the United States. In addition to sodium (Na+), potassium (K+), chloride (Cl−) and citrate ions, the ORS contains a source of carbohydrate, such as glucose, fructose, or dextrose. Typically, the ORS of this invention comprises water, carbohydrate, sodium ions, potassium ions, chloride ions, and citrate ions.

The quantity of sodium ions used in the ORS can vary widely, as is known to those skilled in the art. Typically, the ORS will contain from about 30 mEq/L to about 95 mEq/L of sodium. In a further embodiment, sodium content can vary from about 30 mEq/L to about 70 mEq/, most preferably from about 40 mEq/L to about 60 mEq/L. Suitable sodium sources include but are not limited to sodium chloride, sodium citrate, sodium bicarbonate, sodium carbonate, sodium hydroxide, and mixtures thereof The ORS will also contain a source of potassium ions. The quantity of potassium can vary widely. However, as a general guideline, the ORS will typically contain from about 10 mEq/L to about 30 mEq/L of potassium. In a further embodiment, it may contain from about 15 mEq/L to about 25 mEq/L of potassium. Suitable potassium sources include but are not limited to, potassium citrate, potassium chloride, potassium bicarbonate, potassium carbonate, potassium hydroxide, and mixtures thereof.

The ORS will also contain a source of carbohydrate. The quantity of carbohydrate utilized is important as described above. The quantity must be maintained at less than about 3% w/w, and more preferably about 2.5% w/w or less. Excessive carbohydrate will exacerbate the fluid and electrolyte losses associated with diarrhea, that many cancer patients suffer from.

Any carbohydrate used in prior art oral rehydration solutions may be used to practice the present invention. Suitable carbohydrates include, but are not limited to, simple and complex carbohydrates, glucose, dextrose, fructooligosaccharides, fructose and glucose polymers, corn syrup, high fructose corn syrup, sucrose, maltodextrin, and mixtures thereof.

The ORS will also typically include a source of base. Typically, citrate will be incorporated into the ORS to accomplish this result. Citrate is metabolized to an equivalent amount of bicarbonate, the base in the blood that helps maintain acid-base balance. While citrate is the preferred source of base, any base routinely incorporated into rehydration solutions may be used in the practice of the present invention.

The quantity of citrate can vary as is known in the art. Typically, the citrate content ranges from about 10 mEq/L to about 40 mEq/L, more preferably from about 20 mEq/L to about 40 mEq/L, and most preferably from about 25 mEq/L to about 35 mEq/L. Suitable citrate sources include, but are not limited to, potassium citrate, sodium citrate, citric acid and mixtures thereof.

The ORS will also typically contain a source of chloride. The quantity of chloride can vary as is known in the art. Typically, the ORS will contain chloride in the amount of from about 30 mEq/L to about 80 mEq/L, more preferably from about 30 mEq/L to about 75 mEq/L, and most preferably from about 30 mEq/L to about 70 mEq/L. Suitable chloride sources include but are not limited to, sodium chloride, potassium chloride and mixtures thereof.

Optionally, indigestible oligosaccharides may be incorporated into the ORS. Indigestible oligosaccharides have a beneficial impact on the microbial flora of the GI tract. They help to suppress the growth of pathogenic organisms such as *Clostridium difficile*. These oligosaccharides selectively promote the growth of a nonpathogenic microbial flora. Such ORS's have been described in U.S. Pat. No. 5,733,759, filed Apr. 5, 1995, the contents of which are hereby incorporated by reference.

Typically, the oligosaccharide will be a fructoologosaccharide, an inulin such as raftilose, or a xylooligosaccharide. The quantity can vary widely, but may range from 1 to 100 grams per liter, and more typically from 3 to 30 grams per liter of ORS.

Optionally, the ORS utilized in this invention may contain zinc. The quantity can vary widely, but will typically range from about 0.3 mEq to about 95 mEq of zinc per liter of ORS. Typically, the ORS will contain from about 0.6 mEq to about 3 mEq of zinc per liter. Alternatively, it may contain from about 0.6 mEq to about 1.2 mEq of zinc per liter. The source of zinc ions is not critical. Any zinc salt suitable for human consumption may be used in the ORS of this invention. Examples of suitable zinc sources include zinc gluconate, zinc sulfate, zinc chloride, zinc citrate, zinc bicarbonate, zinc carbonate, zinc hydroxide, zinc lactate, zinc acetate, zinc fluoride, zinc bromide, and zinc sulfonate.

The ORS of the present invention will also typically include a flavor to enhance its palatability, especially in a pediatric population. The flavor should mask the salty notes of the ORS. Useful flavorings include, but are not limited to, cherry, orange, grape, fruit punch, bubble gum, apple, raspberry and strawberry. Artificial sweeteners may be added to complement the flavor and mask the salty taste. Useful artificial sweeteners include saccharin, Nutrasweet®, sucralose, acesulfane-K (ace-K), etc.

Preservatives may be added to help extend shelf life. Persons knowledgeable in the art would be able to select the appropriate preservative, in the proper amount, to accomplish this result. Typical preservatives include, but are not limited to, potassium sorbate and sodium benzoate.

In addition to the carbohydrate described above, the ORS may also contain rice flour, or any other component of rice that is beneficial in the treatment of diarrhea. Numerous rice supplemented ORS's have been described in the literature. Methods for using such rice supplemented ORS's are well known to those skilled in the art. Examples of such rice supplemented ORS's include those described in U.S. Pat. No. 5,489,440 issued Feb. 6, 1996; the contents of which are hereby incorporated by reference.

The ORS's utilized in this invention may also contain amino acids or short peptides. For example, glutamine or derivatives thereof, may be incorporated into the ORS. For example, please refer to U.S. Pat. No. 5,561,111, which is hereby incorporated by reference. Glutamine promotes healing of the gut. The quantity of glutamine can vary but will typically vary from 1 to 100 grams per liter, preferably about 6 grams. If desired ingredients such as glucosamine, chondrotin, hyaluronic acid, etc. can bee added to the ORS in quantities of about 1 to 100 grams per liter.

Arginine, or derivatives thereof, may also be incorporated into the ORS. The quantity of arginine may vary, but will typically range from 1 to 100 gram per liter.

The ORS of this invention can be manufactured using techniques well known to those skilled in the art. As a general guideline, all the ingredients may be dry blended together; dispersed in water with agitation; and optionally heated to the appropriate temperature to dissolve all the constituents. The ORS is then packaged and sterilized to food grade standards as is known in the art. The package may contain labeling indicating that the product is suitable for alleviating mucositis.

ORS may be administered in different forms, depending upon patient preference, as is known in the art. For example, some patients will consume ORS more readily if it is frozen, like a Popsicle®. ORS popsicles are described in detail in U.S. Pat. No. 5,869,459, the contents of which are hereby incorporated by reference. The ORS of this solution may be administered as frozen popsicles if the patient desires such a choice.

ORS's have also been formed into gels in order to enhance patient compliance, especially in a pediatric population. The ORS of this invention may be gelled if desired. Gelled rehydration compositions are described in U.S. patent application Ser. No. 09/368,388 filed Aug. 4, 1999, the contents of which are hereby incorporated by reference. These gels have also been described in PCT Application No. 99/15862.

In summary, the ORS's useful in this invention are well known to those skilled in the art. Any composition that would be considered an ORS, by a medical professional, may be used in the present invention. The key to the present invention is that the inventors have discovered a new use for these ORS's. They have discovered that ORS can be used to alleviate mucositis.

The inventors are using the term "alleviate" to describe two benefits that have been observed to date. First, the ORS reduces the discomfort and pain that the patient experiences from the lesions, ulcers, and sores associated with mucositis. Aside from enhancing the patient's quality of life, the reduced pain enables allows the patient to consume more calories and thus avoids the significant weight loss that is typically associated with mucositis. Further, maintaining a normal diet significantly reduces the potential for the patient to be placed on total parental nutrition (TPN) and the disruptions in life style associated with such invasive therapy.

Secondly, the ORS accelerates the healing process, once the chemotherapy is completed. It has been discovered that the lesions and ulcers heal at an accelerated rate in patients consuming ORS. The exact mechanism by which these benefits occurs is not understood, but the benefits significantly improve the patients quality of life while they are recovering from their cancer. Further, ORS has no known side effects, which further benefits the patients. Thus, the invention is directed to the pallative support of oral mucositis and not to its prevention.

In addition to alleviating ORS, the ORS has other benefits. It helps the patient maintain normal electrolyte levels thru-out their treatment, especially serum potassium levels. Maintaining adequate hydration also helps to fight fatigue.

In order to gain these benefits, it is necessary that the patient consume sufficient quantities of the ORS. The exact quantity required to alleviate the mucositis will vary depending upon the severity of the patient's mucositis, the chemotherapy and/or radiation regimen that the patient is consuming, the patients age, the presence of other diseases besides cancer, etc. However, as a general guideline, at a minimum, the patient should consume at least 500 milliliters daily. The solution can be consumed in one sitting, but it is preferred if the patient gradually consumes the ORS on a periodic basis thru-out the day (i.e., 2–4 times during their waking hours). More preferably, the patient will consume from 1 to 3 liters daily, and most preferably about two liters daily.

ORS therapy can be initiated at any time during the patients chemotherapy. However, the most optimal benefits are obtained if the patient begins consuming ORS prior to the time that chemotherapy or radiation therapy is initiated (i.e. prophylactically). Typically, the patient will begin consuming the ORS about 1 day prior to the initiation of chemo/radio-therapy. More preferably, the ORS therapy will begin about 3 days prior to chemo/radio therapy. Consumption of the ORS should be maintained thru-out the course of chemo-/radio-therapy and maintained until the lesions have healed sufficiently.

It is important to emphasize that while optimal benefits are obtained if ORS consumption is initiated prior to chemotherapy, benefits can still be obtained for mucositis regardless of when therapy is initiated. ORS consumption may be initiated at the same time chemo/radio-therapy is started, during such therapy, or at the conclusion of such therapy Thus the invention should be construed as the use of ORS, at any time, to alleviate mucositis.

The following example is being presented in order to illustrate the invention. It should not be construed as limiting the invention in any manner.

EXAMPLE I

Personal Testimony of Inventor

On January 14$^{th}$, I received a stem cell transplant for Multiple Myeloma at the Mayo Clinic. From day one of chemotherapy through the day of discharge fifteen days following, I consumed two liters of unflavored Pedialyte® daily. I had decided to consume Pedialyte® to accelerate the healing after the destruction of the gatrointestinaltract from the high dose of Melphalan (200 mg/kg) used to ablate the plasma cells. I consumed the first liter prior to breakfast. This hydrated my throat and gave some instant energy that allowed me to consume my breakfast. I consumed my second liter around 5:00 p.m. This was when my energy started to fade. The Pedialyte® gave me another energy boost that allowed me to consume dinner.

I believe my clinical outcome was unique as compared to the other patients I was aware of going through the same treatment. I only required IV fluid one time during my entire stay as compared to almost daily for others. My blood potassium and magnesium levels stayed normal for the entire stay without the need for potassium supplements. Most others required potassium supplements and their magnesium levels did not stay normal. I had no need for hospitalization due to loss of fluid or weight for the entire stay as compared to at least once for most others. I lost no weight either during the stay or in the tow months since (I have gained 10 pounds). The normal is 5–6 pounds loss during the stay and up to another 20 pounds loss in the months following discharge. My total treatment time was 15 days as compared to the average of 21 days.

Even the Mayo Clinic has not come up with anything to speed recovery after such an aggressive procedure. I was told physical recovery post discharge would be 2–3 months. My physical recovery post discharge from everything I can tell was 2–3 weeks.

I claim:

1. A method for alleviating mucositis associated with cancer chemotherapy or radiation therapy comprising the administration to a patient in need thereof, a sufficient quantity of an oral rehydration solution containing
   a. from about 30 mEq to about 95 mEq of sodium per liter;
   b. from about 10 mEq to about 30 mEq of potassium per liter;
   c. from about 10 mEq to about 40 mEq of citrate per liter; and
   d. less than about 3.0% by weight of at least one carbohydrate,
wherein said patient initiates consumption of the oral rehydration solution at least 24 hours prior to the initial chemotherapy or radiation treatment.

2. The method according to claim 1 in which said patient consumes at leas 0.5 liters per day of the oral rehydration solution.

3. The method according to claim 1 in which said patient consumes the oral rehydration solution on a daily basis while undergoing said cancer chemotherapy or said radiation therapy.

4. The method according to claim 1 in which the oral rehydration solution contains from about 0.3 mEq to about 95 mEq of zinc per liter.

5. The method according to claim 1 in which the oral rehydration solution contains from 1 to 100 grams of glutamine per liter.

6. The method according to claim 1 in which the oral rehydration solution.

7. The method according to claim 1 in which said carbohydrate is a mixture of dextrose and fructose.

8. The method according to claim 1 wherein said carbohydrate present in a quantity of less than about 2.5% by weight of the oral rehydration solution.

9. The method according to claim 1 in which said sodium is present in the quantity of about 30 mEq/L to about 70 mEq/L.

10. The method according to claim 1 wherein said sodium is selected from the group consisting of sodium chloride, sodium citrate, sodium bicarbonate, sodium carbonate, sodium hydroxide and mixtures thereof.

11. The method according to claim 1 in which said potassium is present in the quantity of about 15 mEq/L to about 25 mEq/L.

12. The method according to claim 1 wherein said potassium is selected from the group consisting of potassium citrate, potassium chloride, potassium bicarbonate, potassium carbonate, potassium hydroxide and mixtures thereof.

13. The method according to claim 4 in which said zinc is present in the quantity of from about 0.6 mEq/L to about 5 mEq/L.

14. The method according to claim 13 in which said zinc is selected from the group consisting of zinc gluconate, zinc sulfonate, zinc chloride, zinc acetate, zinc sulfate, zinc citrate, zinc carbonate, zinc hydroxide, zinc lactate, zinc fluoride, and zinc bromide.

15. The method according to claim 1 in which the oral rehydration solution contains chloride in the quantity of from about 30 mEq/L to about 80 mEq/L.

16. The method according to claim 15 in which said chloride is selected from the group consisting of potassium chloride, sodium chloride, and zinc chloride.

17. The method according to claim 1 in which said citrate is present in the quantity of from about 20 mEq/L to about 40 mEq/L.

18. The method according to claim 1 in which said citrate is selected from the group consisting of potassium citrate, sodium citrate, and citric acid.

19. The method according to claim 1 in which said patient consumes from about 1 liter to about 3 liters per day of the oral rehydration solution.

20. The method according to claim 6 in which said patient initiates consumption of the oral rehydration solution about 1 week prior to the initiation to said cancer chemotherapy or radiation therapy.

21. A method for alleviating the weight loss associated with cancer chemotherapy or radiation therapy comprising the prophylactic administration to a patient of a sufficient quantity of an oral rehydration solution containing a. from about 30 mEq to about 95 mEq of sodium per liter;

b. from about 10 mEq to about 30 mEq of potassium per liter;

c. from about 10 mEq to about 40 mEq of citrate per liter; and d. less than about 3.0% by weight of at least one carbohydrates;

wherein said patient initiates consumption of the oral rehydration solution at least 24 hours prior to the initial cancer chemotherapy or radiation treatment.

* * * * *